US012383578B2

(12) United States Patent
Berglund et al.

(10) Patent No.: US 12,383,578 B2
(45) Date of Patent: Aug. 12, 2025

(54) CARBAZATE-ACTIVATED POLYVINYL ALCOHOL (PVAC) AS A POLYMER-BASED ANTITUMORAL AGENT

(71) Applicant: CREMED AB (PUBL), Stockholm (SE)

(72) Inventors: David Berglund, New York, NY (US); Erik Berglund, New York, NY (US); Felix Sellberg, Uppsala (SE); Robin Fröbom, Stockholm (SE)

(73) Assignee: CreMed AB, Stockholm (SE)

( * ) Notice: Subject to any disclaimer, the term of this patent is extended or adjusted under 35 U.S.C. 154(b) by 535 days.

(21) Appl. No.: 17/776,643

(22) PCT Filed: Nov. 18, 2020

(86) PCT No.: PCT/SE2020/051105
§ 371 (c)(1),
(2) Date: May 13, 2022

(87) PCT Pub. No.: WO2021/101433
PCT Pub. Date: May 27, 2021

(65) Prior Publication Data
US 2022/0401470 A1 Dec. 22, 2022

(30) Foreign Application Priority Data
Nov. 21, 2019 (SE) .................... 1930380-9

(51) Int. Cl.
| | | |
|---|---|---|
| *A61K 31/785* | (2006.01) | |
| *A61K 45/06* | (2006.01) | |
| *A61P 17/00* | (2006.01) | |
| *A61P 35/00* | (2006.01) | |
| *C08F 116/06* | (2006.01) | |

(52) U.S. Cl.
CPC ............ *A61K 31/785* (2013.01); *A61K 45/06* (2013.01); *A61P 17/00* (2018.01); *A61P 35/00* (2018.01); *C08F 116/06* (2013.01)

(58) Field of Classification Search
CPC ....... A61K 31/785; A61K 45/06; A61P 17/00; A61P 35/00; C08F 116/06
See application file for complete search history.

(56) References Cited

U.S. PATENT DOCUMENTS

| 2011/0008444 A1 | 1/2011 | Bergman et al. |
| 2018/0221495 A1 | 8/2018 | Bowden et al. |

FOREIGN PATENT DOCUMENTS

| CN | 104877158 B | 5/2018 |
| JP | 2016-113374 A | 6/2016 |
| SE | 2050286 A1 | 9/2021 |
| SE | 2050387 A1 | 10/2021 |
| SE | 544131 C2 | 1/2022 |
| WO | 2012/105887 A1 | 8/2012 |
| WO | 2018/172422 A1 | 9/2018 |
| WO | 2019/016189 A1 | 1/2019 |
| WO | 2021/185842 A1 | 9/2021 |
| WO | 2021/204802 A1 | 10/2021 |
| WO | 2021/233534 A1 | 11/2021 |

OTHER PUBLICATIONS

D. Ossipov, et al. "Orthogonal Chemoselective Assembly of Hyaluronic Acid Networks and Nanogels for Drug Delivery," Macromolecules, 46(10), 2013, 4105-4113. (Year: 2013).*
Meyskens Jr., et al. "Cancer Prevention: Obstacles, Challenges, and the Road Ahead," J. Natl. Cancer Inst. (2016) 108(2), 1-8. (Year: 2016).*
Notice of Intent to Grant dated Oct. 15, 2024 from corresponding European Application No. 20816649.6.
Alves, M H et al., Degradable, click poly(vinyl alcohol) hydrogels: characterization of degradation and cellular compatibility, Biomedical Materials, vol. 7, No. 2:024106, 12 pages (2012).
Aulin C. et al., Early stage blockade of the alarmin HMGB1 reduces cartilage destruction in experimental OA, Osteoarthritis and Cartilage, pp. 1-10 (2020).
Fredriksson, F. et al., Sutures impregnated with carbazate-activated polyvinyl alcohol reduce intraperitoneal adhesions, Journal of Pediatric Surgery, vol. 52, No. 11, pp. 1853-1858 (2017).
Ossipov, Dmitri A. et al., Formation of the First Injectable Poly(vinyl alcohol) Hydrogel by Mixing of Functional PVA Precursors, Journal of Applied Polymer Science, vol. 106, No. 1, pp. 60-70 (2007).
Ossipov, Dmitri et al., Orthogonal Chemoselective Assembly of Hyaluronic Acid Networks and Nanogels for Drug Delivery, Macromolecules, vol. 46, No. 10, pp. 4105-4113 (2013).
Takahashi, Haruko et al., Anticancer polymers designed for killing dormant prostate cancer cells, Scientific Reports, vol. 9, No. 1, p. 1096, 11 pages. (Jan. 31, 2019).
Thakore, Sonal I. et al., Exploring potential of polymers in cancer management, Materials for Biomedical Engineering, pp. 113-133, (Jun. 28, 2019).
Zhong, Guansheng et al., Polymers with distinctive anticancer mechanism that kills MDR cancer cells and inhibits tumor metastasis, Biomaterials, vol. 199, pp. 76-87 (Apr. 2019).
Office Action and Search Report from Swedish Priority Application No. 1930380-9, dated May 14, 2020.
Fröbom, Robin, Translational Investigations of Novel and Current Antitumoral Therapies in Gastrointestinal Stromal Tumors, Thesis for Doctoral Degree (Ph.D.), Karolinska Institutet, From Department of Molecular Medicine and Surgery Karolinska Institutet, Stockholm, Sweden, pp. 1-69 (Dec. 13, 2019).
Office Action from corresponding European Application No. 20816649.6 dated Mar. 20, 2023.

(Continued)

*Primary Examiner* — Michael P Cohen
(74) *Attorney, Agent, or Firm* — Porter Wright Morris & Arthur LLP (57) ABSTRACT

The present invention provides a polymer comprising a carbazate-modified polyvinyl alcohol (PVAC) according to Formula I for use in preventing, alleviating, and/or treating cancer, and a method for producing said compound.

7 Claims, 8 Drawing Sheets

(56) References Cited

OTHER PUBLICATIONS

Sellberg, Felix et al., Polyvinyl Alcohol Carbazate as a Polymer-Based Antitumoral Agent, Frontiers in Oncology, vol. 10, Article 598394, pp. 1-14 (Jan. 11, 2021).
Office Action dated Nov. 6, 2024, from corresponding JP Application No. 2022-529788 with machine English translation, 6 pages.

* cited by examiner

CARBAZATE-ACTIVATED POLYVINYL ALCOHOL (PVAC) AS A POLYMER-BASED ANTITUMORAL AGENT

TECHNICAL FIELD

The present invention relates to the field of cancer treatment and provides a composition for preventing, alleviating, or treating cancer.

BACKGROUND

Cancer is one of the leading causes of death worldwide with an estimated 10 million deaths per year. Despite the development of new drugs, resulting in improved patient survival across several cancer types, long-lasting effects are burdened by intrinsic and acquired drug resistance.

Drug development over all is associated with many difficulties until a final product is reached. Initially a promising compound is identified and experimentally tested in different in vitro models, and after that preclinical studies are initiated most often by different mouse models. Many promising compounds/drugs fail to reach the market due to toxicity, severe side effects or manufacturing problems.

A polymer is a substance composed of macromolecules of high relative molecular mass, the structure of which essentially comprises the multiple repetition of units derived, actually or conceptually, from molecules of low relative molecular mass. Polymers constitute a class of chemical compounds that can be modified in several ways. The physical properties of a polymer strongly depend on the length (or equivalently, the molecular weight) of the polymer chain.

In recent years, polymer technologies have been exploited to enhance antitumoral treatments. These applications include using polymers as a drug-delivery system, and integration to the backbone of cytostatic drugs to modify the pharmacokinetic properties (1, 2) and more recently, as direct antitumoral agents (3-5).

These polymers have been designed to interact with cancer cell membrane, due to their relatively net charged membranes (6). Modifications of polymers also allow different sizes, which leads to an enhanced permeability and retention effect (EPR) (7, 8). This leads to an increased extravascular polymer accumulation because of diffusion through permeable and defect endothelial walls of rapidly forming malignant blood vessels (9-11).

Several considerations can be taken to size as well. PVA is known to be non-toxic with both oral and I.V administration and can be secreted via the kidneys (23). Still, as polymeric size increases the clearance kinetics are slowed drastically, PVA at a size of 15 kDa had a $T_{1/2}$ of 90 minutes which was increased to 23 hours after molecular weight was increased to 43 kDa. However, accumulation within tissues remained low (24). When size is increased even further elimination has still been observed up to 125 kDa, well beyond the size of Albumin (67 kDa) a compound normally retained in circulation in healthy individuals, highlighting that molecular mass alone will not predict kidney elimination.

A size-dependent accumulation of polyvinyl alcohol (PVA) in tumor tissue has been described in mice (12). PVA was used as a backbone in a molecule that initially developed to be drug-conjugated, but pilot studies suggested that the polymer possessed direct antitumoral activity.

Carbazate-activated polyvinyl alcohol (PVAC) consists of a PVA backbone, functionalized with carbazate moieties that molecularly targets biological electrophiles such as carbonyls, and PVAC is capable of binding multiple carbonyls. Carbazate contains a neutrophilic nitrogen atom with similar properties to an amine. Compared to an amine carbazate allows for increased stabilization of electrons making it more reactive and the formed bonds more stable. Normally, the excess of such substances is taken care of by reducing agents such as glutathione, or enzymes such as aldehyde dehydrogenase (13).

WO 19016189A1 discloses a composition comprising PVAC for use in prevention or treatment of bacteria-induced infection and disease, WO 2018172422 A1 discloses a composition comprising PVAC for stabilizing erythrocytes, and WO 2012105887 discloses a composition comprising PVAC for treating or preventing inflammatory-related conditions.

In view of the problems discussed above it is a continuous unmet need for alternative treatment strategies with novel modes of action.

SUMMARY OF THE INVENTION

The present invention provides a compound according to Formula I for use in preventing, alleviating, and/or treating cancer, Formula I The present invention also provides a pharmaceutical composition comprising a compound according to Formula I for use in preventing, alleviating, and/or treating cancer.

The present invention also provides a method for preventing, alleviating, and/or treating cancer by administration of a compound as defined in Formula I to a subject in need thereof.

The present invention discloses a compound, i.e., a polymer, comprising a carbazate-modified polyvinyl alcohol (PVAC) according to Formula I for use in preventing, alleviating, and/or treating cancer.

Unmodified repeat units of PVA are denoted with n and carbazate groups conjugated to repeat units are denoted by m.

In one aspect, the degree of polymerization (DP) of the polymer for use according to formula I of the present invention is in the range of $25 \leq DP \leq 3000$. In another aspect the degree of polymerization (DP) of the polymer for use according to formula I of the present invention is in the range of $100 \leq DP \leq 2,000$. In another aspect the degree of polymerization (DP) of the polymer for use according to formula I of the present invention is in the range of 100≤DP≤1200. In yet another aspect the degree of polymerization is (DP) of the polymer for use according to formula I of the present invention is in the range of 100≤DP≤600.

In one aspect the polymer for use according to the present invention (Formula I) has a degree of substitution (DS) of carbazide in the range of 1 to 50%. In another aspect the polymer for use according to the present invention has a degree of substitution (DS) of carbazide in the range of 1-20%. In another aspect the polymer for use according to the present invention has a degree of substitution (DS) of carbazide in the range of 10%. In another aspect the polymer for use according to the present invention has a degree of substitution (DS) of carbazide in the range of 0.5 to 50%. In another aspect the polymer for use according to the present invention has a degree of substitution (DS) of carbazide in the range of 2.5-20%. In another aspect the polymer for use according to the present invention has a degree of substitution (DS) of carbazide in the range of 10%.

In one aspect the polymer for use according the present invention and described above, has a carbazate content in the range of 0.5-10 mmol/g polyvinyl alcohol carbazate. In another aspect the polymer for use according the present invention has a carbazate content in the range of 2-8 mmol/g polyvinyl alcohol carbazate. In another aspect the polymer for use according the present invention has a carbazate content in the range of 2-6 mmol/g polyvinyl alcohol carbazate.

In another aspect the polymer for use according to the present invention and described above has a carbazate content in the range of 0.1-10 mmol/g polyvinyl alcohol carbazate, In another aspect the polymer for use according to the present invention has a carbazate content in the range of 0.5-4 mmol/g polyvinyl alcohol carbazate. In another aspect the polymer for use according to the present invention has a carbazate content in the range of 2 mmol/g polyvinyl alcohol carbazate.

In yet another aspect, the polymer for use according to the present invention, has a weight-average molecular weight in a range of from about 1,000 Daltons to about 150,000 Daltons.

All aspects of the polymer according to Formula I described above are combinable in different embodiments.

The present invention also provides a pharmaceutical composition comprising said compound(s) or polymer(s) according to Formula I as described above for use in preventing, alleviating, or treating cancer.

The pharmaceutical composition comprises a polymer of Formula I of the present invention also described in the detailed description, for use in preventing, alleviating, or treating cancer.

The pharmaceutical composition for use according to the present invention may, further comprise a pharmaceutically acceptable excipient or carrier. The acceptable carrier may for example be an aqueous solution. In one aspect the aqueous solution is water.

The pharmaceutical composition for use according to the present invention may be in the form of a lyophilizate. The lyophilizate may be reconstituted in an aqueous solution before administration to a subject in need thereof.

The cancer may be a solid, liquid or heamatological tumor. In one aspect the cancer is selected from melanoma, gastrointestinal cancer, T-cell lymphoma, B-cell lymphoma and Hodgin's lymphoma.

The polymer or the pharmaceutical composition for use in preventing, alleviating, and/or treating cancer as defined above, where the use comprises to administrate a therapeutically effective amount of the polymer according to Formula I or the pharmaceutical composition to a subject in need of such treatment.

A further object is to provide a method for preventing, alleviating, and treating cancer comprising administering a therapeutically active amount of the compound according to Formula I or a pharmaceutical composition comprising said compound according to the present invention.

The cancer may be selected from melanoma, gastrointestinal cancer, T-cell lymphoma, B-cell lymphoma and Hodgin's lymphoma.

In one aspect the method for treating cancer in a subject comprises to administrate a pharmaceutically effective dose of the polymer according to the present invention or the pharmaceutical composition defined above to a subject in need of such treatment.

The route of administration may be parenteral, intravenous, infusion, and/or peroral. In one aspect, the administration route is parenteral. In another aspect the route of administration is intravenous. In yet another aspect, the administration route is via infusion. In another aspect, the administration route is peroral.

In yet another aspect, the use of the polymer or pharmaceutical composition of the present application defined above in a method for treating cancer may be in combination with another anticancer treatment.

DETAILED DESCRIPTION

It is to be understood that this invention is not limited to particular configurations, process steps, and materials disclosed herein as such configurations, process steps, and materials may vary somewhat.

It is also to be understood that the terminology employed herein is used for the purpose of describing particular embodiments only and is not intended to be limiting since the scope of the present invention will be limited only by the appended claims and equivalents thereof.

All references cited are incorporated herein by reference in their entirely and for all purposes to the same extent as if each individual publication or patent or patent application was specifically and individually indicated to be incorporated by reference in its entirety for all purposes.

The present invention is best understood by reference to the following definitions, the Figures and exemplary disclosure provided herein.

In this specification, unless otherwise stated, the term "pharmaceutically acceptable excipient" means a non-toxic, inert solid, semi-solid or liquid filler, diluent, encapsulating material, or formulation auxiliary of any type.

In this specification, unless otherwise stated, the term "pharmaceutically active compound" encompasses any substance that will produce a therapeutically beneficial pharmacological response when administered to a host, including both humans and animals.

In this specification the term "administering", or "administration" means providing a drug to a subject in a manner that is pharmacologically useful.

In this specification, unless otherwise stated, the term "cytotoxic compound" refers to a compound that has the ability of arresting the growth of, or killing, cells, i.e., having high cytotoxic activity.

In this specification the term "cancer" is meant to mean any malignant neoplastic disease, i.e. any malignant growth or tumor caused by abnormal and uncontrolled cell division. The term "cancer" is meant to include both solid, localized tumors, and non-solid cancer forms. For example said cancer forms may be selected from the group consisting of leukemia (ALL, AML, CLL, CML, CMML), T-cell leukemia, multiple myeloma, ovarian carcinoma, prostate cancer, cervix adenocarcinoma, squamous cell carcinoma, breast cancer, colorectal cancer, small bowel cancer, anal cancer, gastric cancer, kidney cancer, malignant melanoma cancer of the renal pelvis and ureter, urethral cancer, bladder cancer, liver cancer, appendix cancer, pancreas cancer, lung cancer, cancer of the oesophagus, lip/oral cavity cancer, nasal cancer, larynx cancer, brain/central nervous system cancer, skin cancer, thyroid and thymus cancer, sarcoma, head and neck cancer, Non-Hodgkin lymphoma (NHL), Hodgkin lymphoma, and pseudomyxoma peritonei.

In the present invention the term PVAC means Carbazate activated Polyvinyl alcohol, Carbazate modified Polyvinyl alcohol, Polyvinyl alcohol carbazate, having the chemical name Poly[1-hydroxyethylene)-ran-(1-hydrazinecarboxylatoethylene)].

The degree of substitution (DS) of a polymer is the (average) number of substituent groups attached per base unit (in the case of condensation polymers) or per monomeric unit (in the case of addition polymers).

The degree of polymerization (DP) is the number of monomeric units in a macromolecule or polymer or oligomer molecule.

Initially, PVAC was supposed to act as a crosslinker to form hydrogels that would be rather inert. However, initial results when working with cell lines in relation to the compound yielded interesting morphological results. This spurred the inventors to further investigate the substance PVAC in a tumor system.

Herein, an experimental model of tumors of different cellular origin was used and combining it with mouse models with different immune functions.

An immunocompetent B16.F10 melanoma model, and an athymic breast cancer MB-MDA-13 model was used to investigate the antitumoral effects and the safety of intra tumoral PVAC injections.

EXAMPLES

1. Materials and methods
1.1 Compounds

PVAC was synthesized by Specific Polymers (Castries, France). PVAC was stored freeze-dried at −20° C. and dissolved in desired medium immediately prior to the different experiments. As controls ethyl carbazate (EC, a low molecular weight carbazate compound) and PVA (at the same size as the one used in PVAC synthesis) were used. The degree of polymerization was 295≤DP≤522, the carbazate content was 4±2 mmol/g. The polymer is very soluble in water, practically insoluble in ethanol, and the distribution of substituents was random. EC and PVA were dissolved in deionized water yielding stock concentration of 50 mg/m L. Both compounds were purchased from Sigma.

1.1.1 Synthesis of Carbazate-Modified Polyvinyl Alcohol (PVAC)

To 0.50 g of polyvinyl alcohol (PVA, average molecular weight 16 kDa) was added 20 ml dimethyl sulfoxide (DMSO). The mixture was heated at 80° C. for 15 min to completely dissolve PVA. After cooling to room temperature, 1.00 g of 1, 1'-carbonyldiimidazole (CDI) was added and the mixture was stirred for 24 h. Hydrazine hydrate, 3.2 ml (80%), was added to the mixture, which was left to stir for another 24 h. The reaction mixture was diluted with water and dialyzed (Spectra/Por® 6 Dialysis Membrane, molecular weight cut-off, MWCO, 3.5 kDa) for three days and the product was isolated as a white powder after lyophilization.

Characterization: The degree of substitution (DS) of carbazate groups was investigated by 2,4,6-trinitrobenzene sulfonic acid, 5% (w/v) in $H_2O$ (Sigma) assay. One ml samples were dissolved in 20 ml sodium tetraborate decahydrate (k99.5%, Sigma) buffer (pH 9.3, 0.1 M). From the prepared solutions, 1 ml was mixed with 25 pl2,4,6-trinitrobenzene sulfonic acid solution. After three hours of reaction the mixture was analyzed by ultraviolet-visible spectroscopy at 505 nm and compared to a standard curve based on tert-butyl carbazate (1.98.0%, Sigma). The degree of substitution was calculated to be 7.5% (0.075).

1.2. Hydrophobicity and Hydrophilicity Assay (QCM-D)

To study the hydrophobic and hydrophilic interactions of PVA and PVAC QCM-D was used. Gold sensors (Biolin Scientific, Sweden) were coated with 1-undecanethiol (Sigma) in a self-assembling monolayer, to form a hydrophobic surface and uncoated gold sensors were used as a hydrophilic surface. They were then washed in type-1 water and dried with $N_2$ gas. The sensors were then placed in a QSense Pro (Biolin Scientific), the experiment was initiated with PBS being passed over the sensors for 5 minutes followed by PBS containing 2.5 mg/mL of PVAC or PVA for 45 minutes and finally 10 minutes of PBS. Mass shift (ng/cm$^2$) and dissipation was recorded. Two hydrophilic and hydrophobic sensors were run in two experiments resulting in 4 observations per surface.

The mass shift from PBS was neglible for both surfaces (4.0±7.8 ng/cm$^2$). On the hydrophobic sensors the mass shift was low for both PVAC (31.8±4.5 ng/cm$^2$) and PVA (13.8±13.6 ng/cm$^2$). On the hydrophilic sensors the mass shift was rapid and high for both PVAC (179.2±28.6 ng/cm$^2$) and PVA (262.7±52.9 ng/cm$^2$) recorded one minute after start of circulation with solutions containing the polymers. The final recording, after 10 minutes of washout was significantly lower for PVAC (198.8±22.6 ng/cm$^2$) compared with PVA (414.2±6.8 ng/cm$^2$). Dissipation was also lower for PVAC (1.2±0.02) compared to PVA (2.1±0.00). In combination this indicates that the PVA was able to form a tighter layer as more molecules were packed on the surface, this reorientation was also a slower progress as the mass density on the sensor increased 60% over the time PVA containing solution circulated after the initial occupation.

1.3 Cell Lines

GIST-T1 is a human gastrointestinal stromal tumor (GIST) cell line, purchased from Cosmo Bio Co. Ltd. (Tokyo, Japan). B16.F10 (murine) and A375 (human) are both melanoma cell lines. A375 was purchased from ATCC (Manassas, Va., USA) while B16.F10 was a kind gift from Adlego AB (Stockholm, Sweden), which also used the MD-MBA-13 cell line in mouse model. Cells were maintained in DMEM medium supplemented with 10% FBS, 1% penicillin/streptomycin. In addition, GIST-T1 was supplemented with 1% Glutamax. Cells were cultured in an incubator, at 37° C. and 5% $CO_2$. GIST-T1 was used for viability experiments and flow cytometry while B16 and A375 were used only for flow cytometry experiments.

1.4 Cell Viability Assay $0.25 \times 10^4$-$1 \times 10^4$ GIST-T1 cells were seeded into each well in a 96-well plate. PVAC, EC, and PVA were added into each well or vehicle (deionized water) with subsequent incubation for 24 or 48 hours. CellTiter-Glo assay (Promega, MI, USA) is an ATP-based luminometric method that was performed according to protocol. In brief, cells were removed from incubator to allow adjust to room temperature after which 100 μL of room temperature CellTiter-Glo was added to each well. The plates were put on a shaker for 5-10 min. Cells rested for 5-10 min before measurement on an EnVision 2103 Multilabel Reader (Perkin Elmer, MA, USA).

Medium was prepared with the addition of PVAC in 6 different concentrations with dilutions of a factor of 5 (2.5 mg/mL to 0.8 μg/mL). Cells were kept in culture for 48 hours for B16 and GIST-T1, for A375 media was replaced after 48 hours with media containing new PVAC at the same concentration as previously or media without the addition of PVAC to investigate if the effect of PVAC could be washed out. The cells were then cultured for another 48 hours. Wells were harvested daily and then they were analysed by flow cytometry for viability and cell cycle analysis.

1.5 Flow Cytometry

For apoptosis flow cytometry cells were harvested and washed twice in PBS, resuspended in Annexin Binding Buffer (10 mM HEPES, 150 mM NaCl, 2.5 mM $CaCl_2$) in PBS), and transferred to glass flow cytometry tubes to which 5 μl of Annexin V FITC (Sigma, MI, USA) and 10 μl of 7-AAD (Sigma, MI, USA) or PI (Thermofisher, MA, USA) was added. The samples were incubated for 20 minutes prior to analysis. GIST-T1 cells were seeded at $3.75 \times 10^5$ cells/well in a 6-well plate and harvested and stained as above. A375 and B16 were cultured in 24-well plates seeded with $1 \times 10^5$ cells per well, the cells were allowed to settle for 24 hours before media was changed to contain PVAC, they were harvested and stained as described above. Samples were analysed on an Accuri C6 (B16) or FACSverse flow cytometer (A375 and GIST-T1) (BD, Franklin Lakes, N.J., USA). All samples were exported as FSC files and processed in FlowJo (FlowJo LCC, Ashland, Oreg., USA). Gating strategies can be seen in representative examples in the results section for each technique. For cell cycle analysis built in tool in FlowJo was used with the Watson (Pragmatic) univariate model. In parallel to flow cytometry experiment, images of cells in culture were also taken each day with Samsung A3 cellular device (Seoul, South Korea).

1.6 In Vivo Model of Melanoma and Breast Cancer

This part of the study was performed by Adlego AB, at Astrid Fagreaus Laboratory, in two parts. The first part encompassed 36 immunocompetent C57BL/6J mice injected with B16.F10 cells. The second part encompassed 36 athymic nude mice injected with MDA-MB-231 tumor cells. Following injection of B16.F10 cells into the C57BL/6J mice the animals were monitored twice weekly recording weight, general health and tumor size. When the tumors size had reached at least 50 μL the animals were stratified into three groups of 12 mice per group based on tumor size. All three groups of C57BL/6J mice were subjected to intra/peri tumoral injections three times per week at a volume of 100 μL per injection for the duration of the study period. One group served as a control group and received NaCl (vehicle) injections, the other two groups received different doses of PVAC, 0.5 and 10 mg/mL, respectively. These dosages originated from in vitro experiments, with effects observed at 0.5 mg/mL and also a high-dose group with 10 mg/mL. Tumor size and health status were recorded three times weekly during the treatment period. Animals were euthanized when average tumor size of the control group reached 2 mL in volume. Tumors were then excised weighed and divided into two parts. One part was frozen in isopentane on dry ice and stored at −80° C. the second part was placed in 4% buffered formaldehyde until shipment to Micromorph AB (Lund, Sweden) for immunohistochemical analyses.

Following injection of MDA-MB-231 cells into athymic nude mice the animals were monitored twice weekly recording weight, general health and tumor size. When the average tumor size was approximately 100 μL the animals were stratified into three groups of 12 mice per group based on tumor size. All three groups were subjected to 28 days of twice-weekly intra/peri tumoral injections at a volume of 100 μL per injection. One group served as a control group and received NaCl (vehicle) injections. The remaining two groups received different doses of PVAC, as described above. The animals were euthanized on Day 29 and the tumors were excised, weighed, and divided into two parts handled as described above.

1.7 Immunohistochemistry and Histology

Sectioning and staining of tumors was carried out by Micromorph AB. All sections were dehydrated, cleared, and infiltrated with paraffin automatically in a TISSUE-TEK V.I.P (Miles Scientific, Newark, Del., USA). Sections were acquired from peripheral and central parts of the tumors. All tumors were stained with haematoxylin eosin (HE). Sections from B16 were also stained with anti-CD3 and anti-KI67 (see Table 1). HE-staining was carried out with Mayer's haematoxylin (Bio-Optica, Milano, Italy) for 6 minutes followed by washing in running water for 10 minutes. Then staining in eosin (Bio-Optica) for 3 minutes followed by washing in distilled water, finally they were dehydrated and mounted.

TABLE 1

Antibodies used for immunohistochemistry

| Target | Type | Source |
|---|---|---|
| Anti-CD3 | Rabbit monoclonal | Abcam, ab16669 |
| Anti-KI67 | Rabbit monoclonal | Abcam, ab16667 |
| Secondary antibody | Bright Vision anti-rabbit/HRP | Immunologic |

Slides used for immunohistochemistry were first deparaffinated before antigen retrieval by boiling in boric acid (pH 8.0)+0.2% triton-X 100 for 20 minutes. The slides could cool at room temperature for 20 minutes and then washed in PBS. They were incubated with primary antibodies for 1 hour (see Table 1) in PBS with 5% goat serum (Jackson Immunoresearch, Cambridgeshire, UK), followed by washing three times in PBS. Secondary antibody was added (see Table 1) and slides were incubated for 30 minutes, followed by washing three times in tris buffer and incubation in 3,3-Diaminobenzidine for 5 minutes. Finally, they were rinsed in distilled water and counter stained in haematoxylin for 5 seconds before dehydration and mounting.

A senior pathologist scored all tumor slides in a blinded fashion using a Leica DMRX microscope. B16 was scored with regards to tumor morphology, amount of CD3+ cells and KI67 expression. The scoring of CD3+ cells and Ki67 expression was: 0 (no positive cells); very few positive cells (0-1+); few positive cells (1+); few to moderate numbers of positive cells (1-2+); moderate number of positive cell (2+); moderate to high number of positive cells 2-3+); high numbers of positive cells (3+); MDA-MB-231 was scored with regards to tumor morphology and leukocyte infiltration.

1.8 Cell Cycle Analysis

For cell cycle flow cytometry samples were washed ×2 in PBS and then resuspended in 500 µl of PBS, the entire volume of PBS was then added to 4.5 mL of ice cold 70% EtOH and the samples were then fixated for a minimum of 2 hours (all samples were analyzed within 48 hours) on ice or at 4° C. Samples were then centrifuged at 500 g×5 min and supernatant EtOH discarded, cells were resuspended in 5 mL of PBS and centrifuged at 500 g×5 min and supernatant PBS discarded. Finally, cells were resuspended in 1 mL of PI staining buffer containing 10 µg/mL of PI (Sigma) and 100 µg/mL of RNase (Sigma) and transferred to glass flow cytometry tubes, samples were incubated for 30 minutes prior to analysis and analyzed within 60 minutes.

Flow Cytometry cell cycle analysis assay from cell culture of A375 human melanoma, three cultures from different passages in triplicates.

1.9 Statistics

Graphs are depicted with the mean value and error bars as standard deviation, significant differences (p value <0.05) are denoted with * in graphs. Statistics in text are reported as p value, mean difference between groups tested, 95% CI (when possible to calculate), in the format of, p=0.05, z % (x-y), were z is the mean difference between the groups and xy are the bounds of the 95% CI. Multiple group analyses were carried out using one parameter one-way ANOVA for parametric data (e.g. tumor weight) and Kruskal-Wallis for non-parametric data (e.g. lymphocyte invasion). Two-way ANOVA was used to analyse two parameter data sets (e.g. tumor size over time). ANOVA was followed with multiple comparisons testing between the experimental groups and the control group using Tukey's in the case of one-way ANOVA and Dunnett's in the case of two-way ANOVA. When possible, technical replicates were tested in the analysis, when this was not possible the mean from the replicates was used instead.

2. Ethical Permits

In vivo studies with B16 and MDA-MB-231 were conducted with permit N37/15 by the regional animal experimental ethics committee in Stockholm North.

3. Results 3.1 PVAC, PVA and EC Effect on Cell Viability

Figure 1:
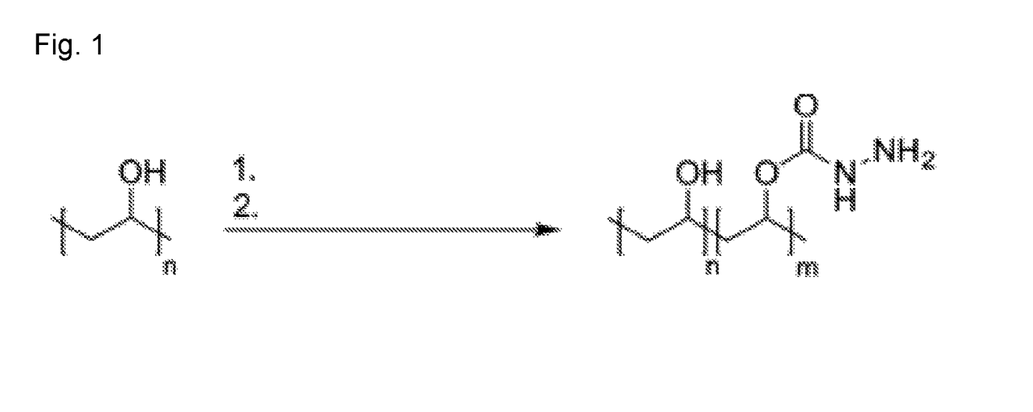
FIG. 1 shows the synthesis of the PVAC-molecule comprising the polymer functionalized with multiple carbazate groups.
Figure 2A:
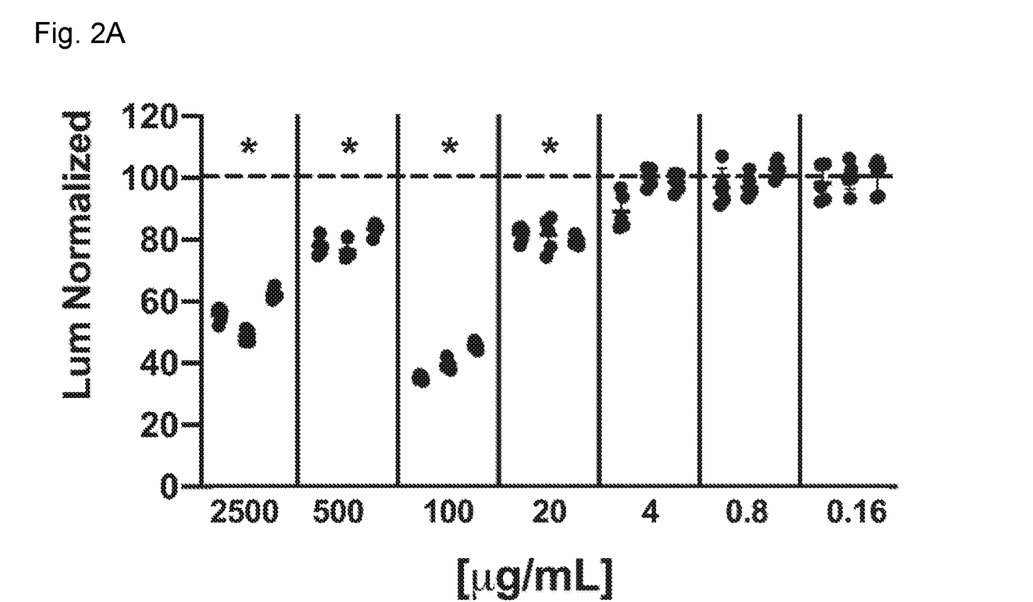
FIGS. 2A-C show a graph illustrating the effect of PVAC (A), EC (B) and PVA (C) on cell viability.

Addition of PVAC to the cell culture resulted in a reduction of ATP in the wells reflecting a reduced number of viable cells. The effect did not follow a linear response curve; instead, a peak concentration was observed around 100 µg/mL. At concentrations below 20 µg/mL no reduction in viable cells was observed (FIG. 2A).

Figure 2B:
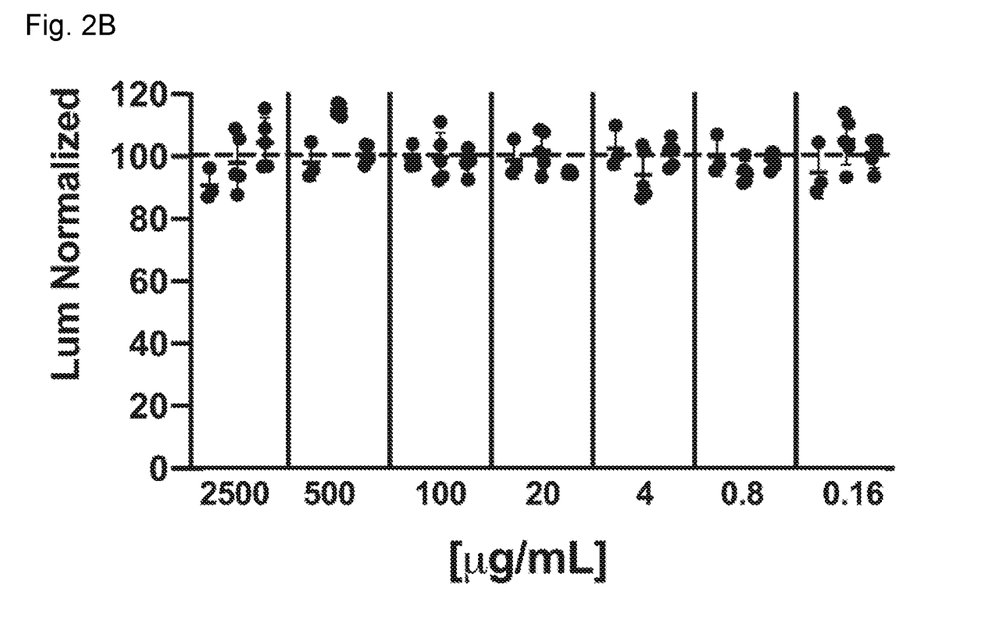
Figure 2C:
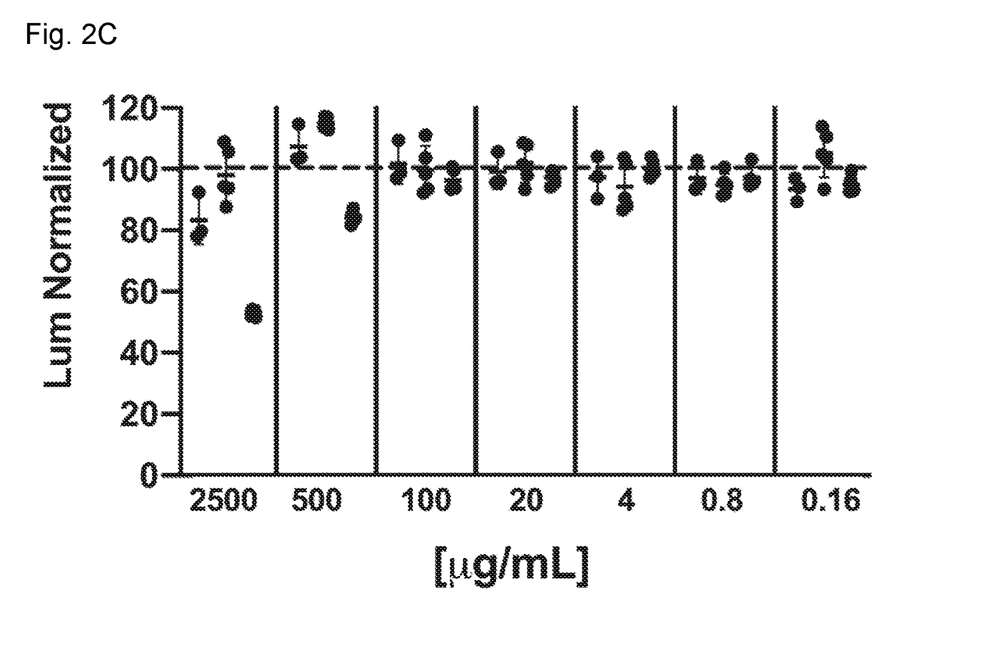

To assess the potential cytotoxicity from the chemical constituents of PVAC, the backbone PVA (FIG. 2C) at the same size as the synthesized PVAC and a low molecular weight carbazate, ethyl carbazate (EC) (FIG. 2B) was used at different concentrations. The two compounds did not reduce cellular viability at biologically relevant concentrations, indicating that the combination of the carbazate group with a large backbone is needed to observe the effects of PVAC. The carbazate content in molar mass in ethyl-carbazate is roughly 5 times as high as in PVAC; therefore, the carbazate content is the same in 2500 µg/mL PVAC and 500 µg/mL ethyl-carbazate.

Figure 3A:
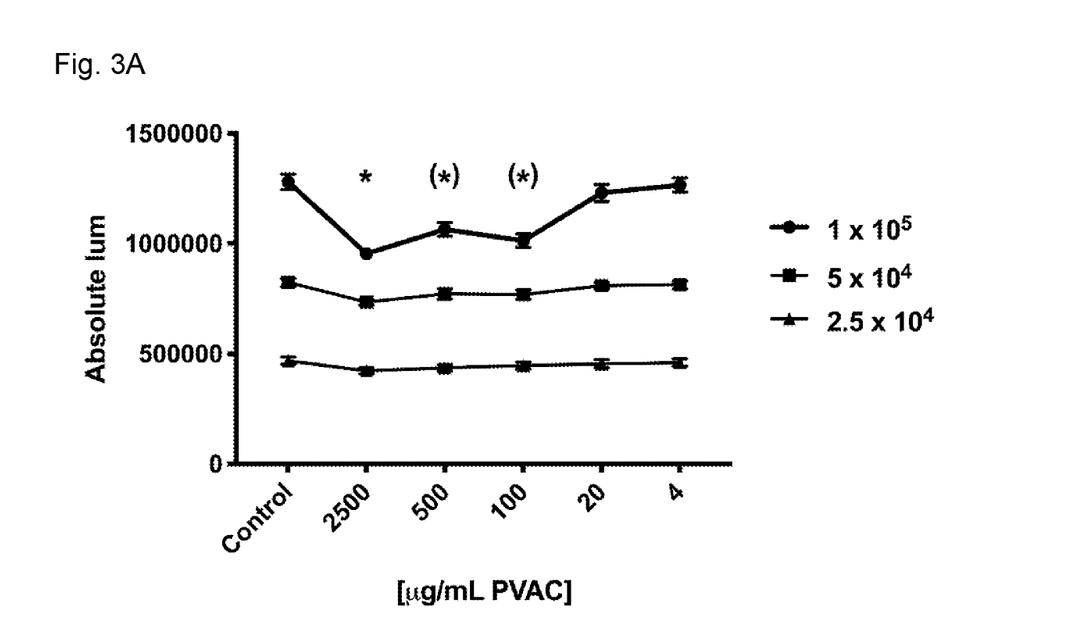
FIGS. 3A-B show a graph illustrating cell viability of cells seeded at different cell densities after 24 h (A) and 48 h (B), respectively.
Figure 3B:
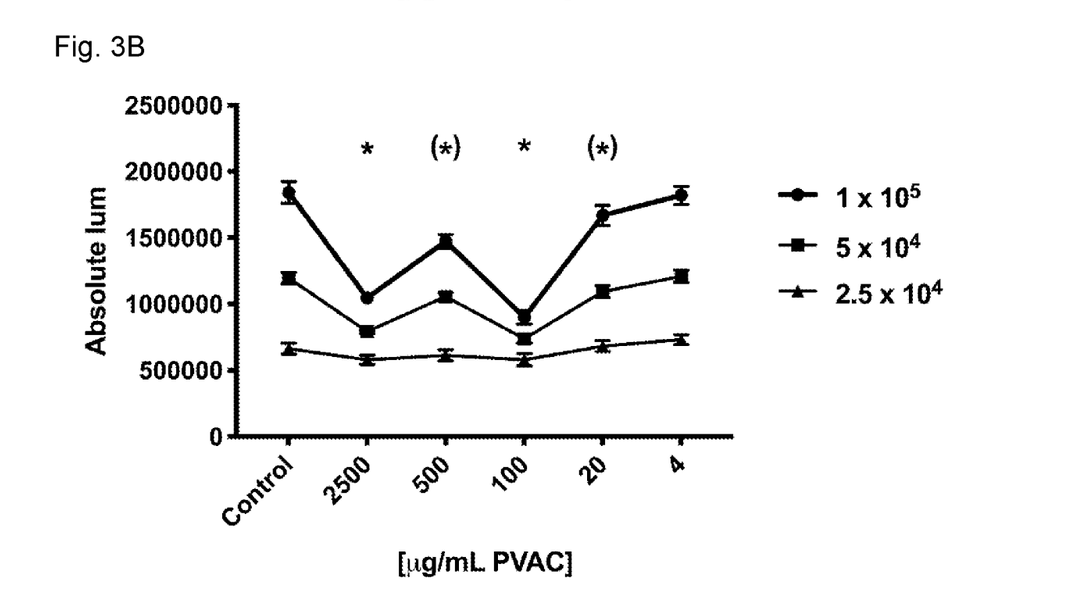

FIGS. 3A and B show cell viability of cells seeded at different cell densities after 24 h (A) and 48 h (B), respectively. Increased density of cells resulted in a decrease in cell viability. The effect was most pronounced with high seeding density after 48 h (B), indicating that the cell viability reduction upon PVAC treatment is dependent on both time and seeding density. The non-linear dose-response relationship was observed in high seeding density at both time intervals, while for medium density ($5\times10^4$) cells/well) only at 24 h (A). The use of absolute luminescence also shows increased values between 24 h and 48 h, indicative of viable and proliferating cells.

The effect of PVAC on cell viability on different cell lines was also tested with similar results. The cell lines tested represent melanoma, T and B-cell lymphoma, gastrointestinal stromal tumor and Hodgkin's lymphoma (See Table 2).

TABLE 2

| Cell lines | Species | Cancer type |
|---|---|---|
| B16F10 | Mouse | Melanoma |
| A375 | Human | Melanoma |
| GIST-T1 | Human | GIST |
| Jurkat 45.01 | Human | T cell lymphoma |
| Daudi | Human | B cell lymphoma |
| HDLM-2 | Human | Hodgkin's lymphoma |

3.2 Flow Cytometric Evaluation of Cell Viability Using Annexin V/7-AAD or PI

Figure 4A:
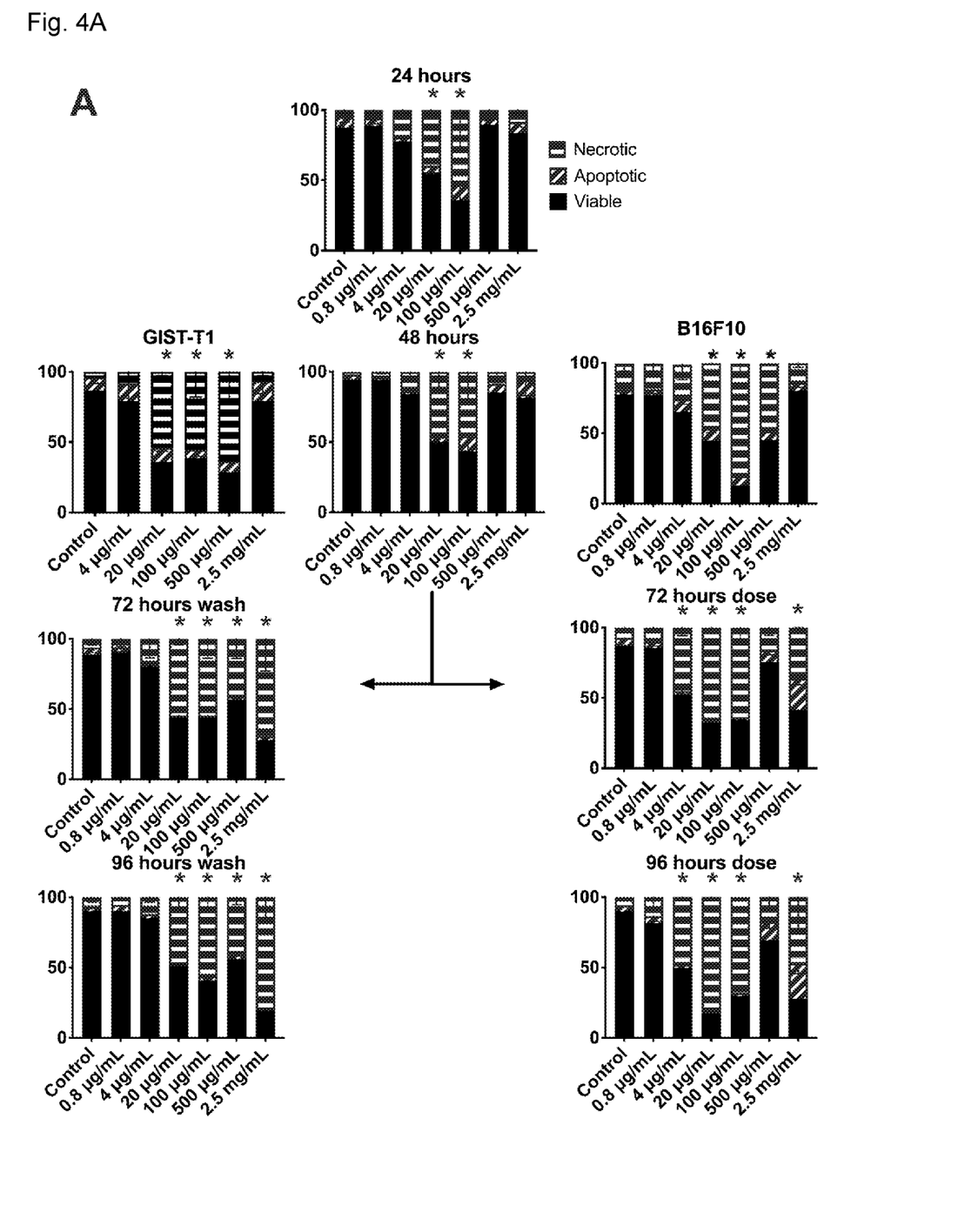
FIGS. 4A-C show flow cytometric evaluation of cell viability in different cell lines and incubation times (A), morphological evaluation of cultured cells (B), and images of collapsed washout cells and dosed cells (C).

Flow cytometric evaluation using Annexin V/7-AAD or PI was used to assess cell viability, apoptotic and necrotic cells (see FIG. 4A). A375 human melanoma cells were used in an extended protocol, assessing the possibility to rescue cells from PVAC treatment. GIST-T1 cells and B16.F10 cells were assessed after 48 h. After 48 h, most cells (A375, B16 and GIST-T1) displayed a statistically significant increase in late apoptotic/necrotic cells in PVAC concentrations ranging from 20-500 µg/mL. The effect was not significant for other concentrations.

To assess the possibility of rescuing cells by either dosing new PVAC (right panels) or washing cells and continue growing them in cell medium (left panels) the higher concentrations 500 µg/mL and 2.5 mg/mL display an increased number of dead cells and a reduction in viable cells after 72 and 96 hours in culture. After dosing the highest concentration (2.5 mg/mL) as well as a lower concentration (4 µg/mL) had an increased number of dead cells and a reduction in viable cells after 72 and 96 hours in culture.

Figure 4B:
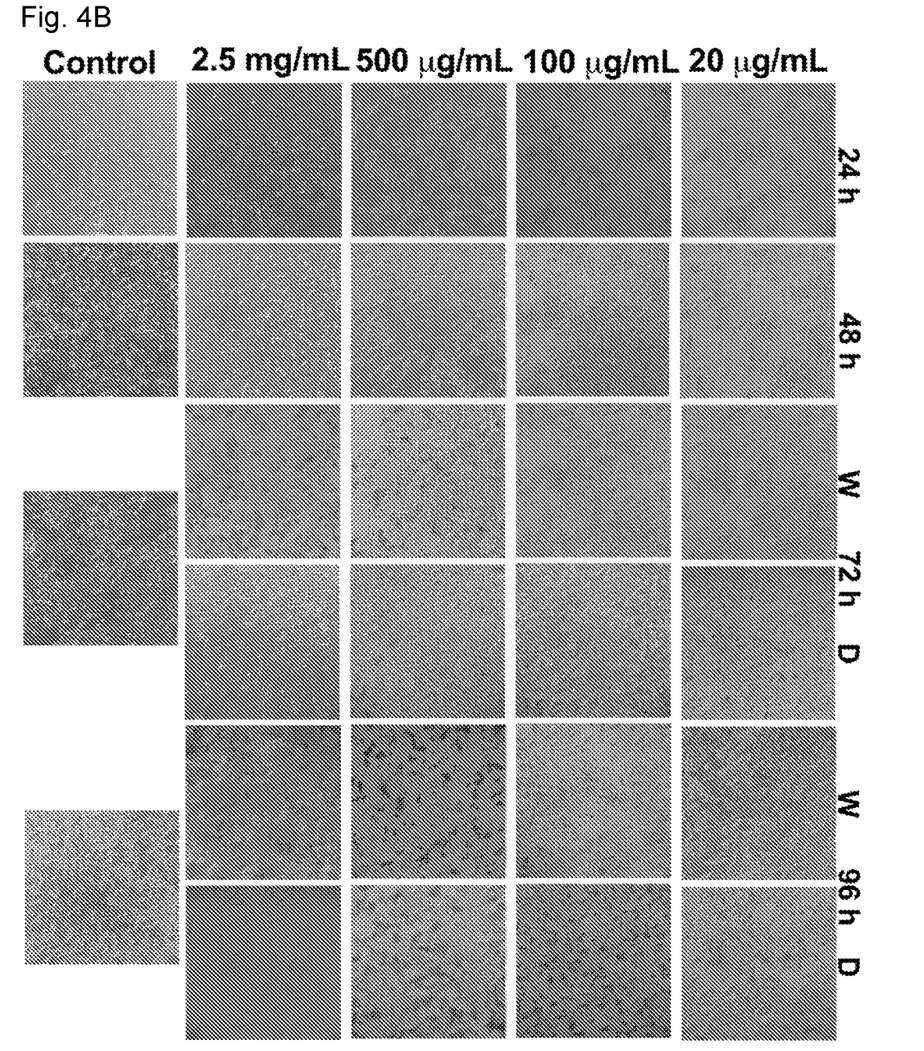

3.3 Morphological Evaluation of Cultured Cells Exposed to PVAC or Vehicle is Shown in FIG. 4B.

The control increased rapidly in confluency during culture with cells growing initially in a monolayer but later also in multiple layers. Changes in the visuals of the culture was observed during the first day after exposure to PVAC. Confluency and morphology appeared affected in the cells with 20 and 100 µg/mL PVAC. In addition, cells exposed to 500 µg/mL PVAC also displayed apoptotic bodies morphologically. After 48 hours in culture the effects are similar with increased confluency. After wash-out the cells exposed to 2.5 mg/mL collapses into an unrecognisable mass of necrosis, 500 μg/mL also appeared more affected after wash-out while 20- and 100 μg/mL slowly recovered in confluency and morphology. After dosing 2.5 mg/mL cells kept their gross morphology initially but after 96 hours in culture cells appeared deformed. 20-500 μg/mL appeared increasingly affected over time with large masses of apoptotic/necrotic debris.

Figure 4C:
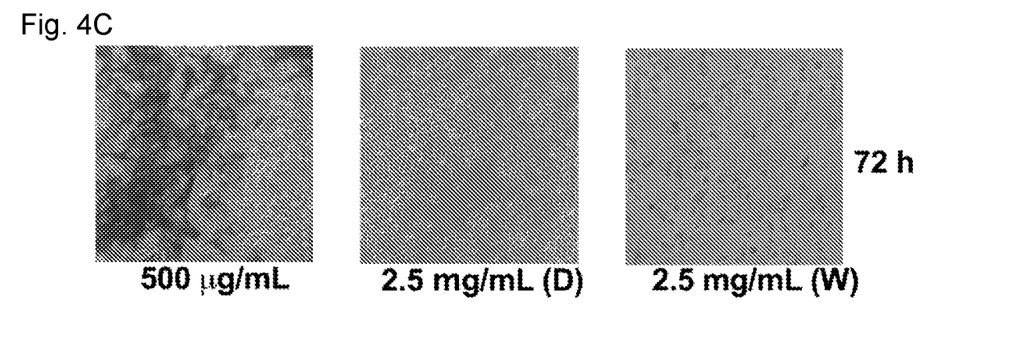

FIG. 4C display images of the same phenomenon as observed previously in 2.5 mg/mL PVAC where the washout cells collapsed, and the dosed cells kept intact morphology. The left image depicts crosslinking of cellular remains into large sheets, potentially a direct effect by PVAC. The crosslinking effect was most evident at 100- and 500 μg/mL but did not occur at lower or higher concentrations. As the solubility of PVAC is affected when more carbazates are bound, another possible explanation is that precipitation of PVAC (FIG. 4C) was observed.

Figure 5A:
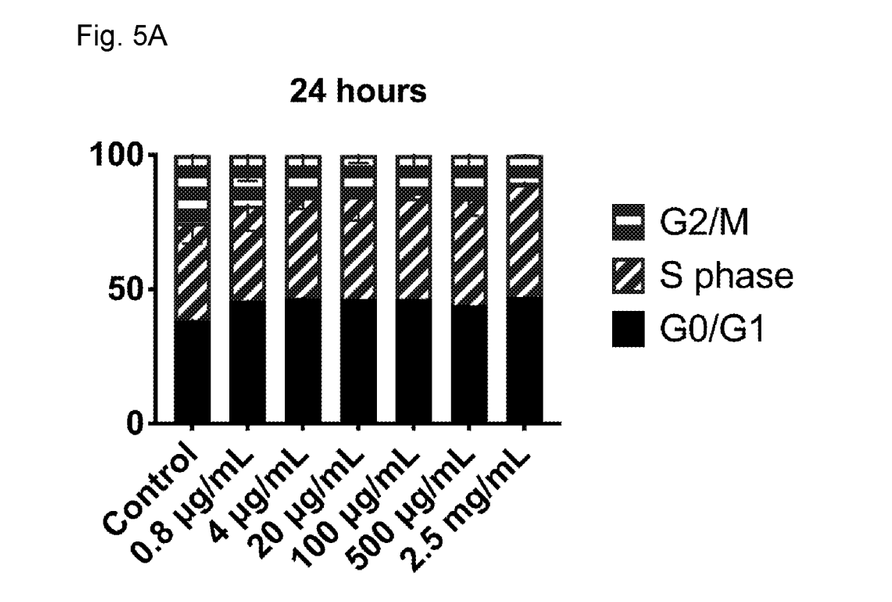
FIGS. 5A-B show flow cytometric evaluation of the cell cycle before, after PVAC treatment 24 and 48 hrs.
Figure 5B:
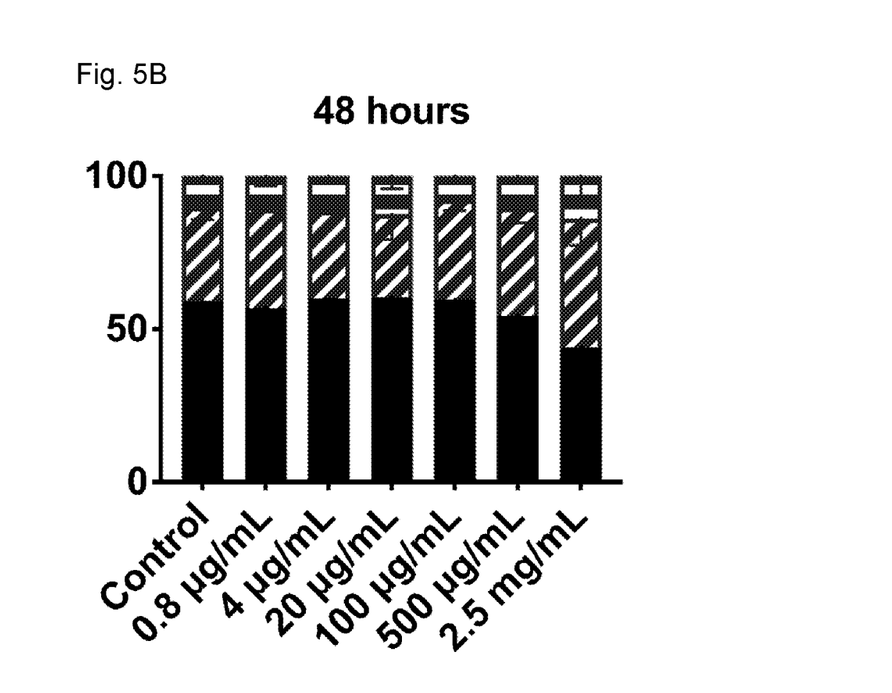

There was no difference between the control and PVAC treated cells on the cell cycle during the culture, as shown in FIG. 5A-B.

Representative of example of gating strategy, single cells were identified using SSC W/H and FSC W/H gates and then analyzed with FlowJo cell cycle analysis tool. Bars represent different treatments and graphs represent timepoints. Distribution of phases in cell cycle represented with different colors. Confluency over time in culture as judged from visual inspection in the control and 2.5 mg/mL. A non-linear dose response was evident in both viability assays, morphology and with apoptosis flow cytometry (data not shown). This effect did not seem to be cell line specific. The concentration of PVAC shows a peak effect (100 μg/mL) in vitro was chosen for evaluating the effect in vivo. 10 mg/mL was also chosen to make sure it was a saturating dose that still showed potent effects.

3.4 In Vivo B16 and MDA-MB-231 is Shown in FIGS. 6A-D

C57BL/6J mice were inoculated with B16 tumours and subjected injection into the tumour with PVAC (a high or low dose) or vehicle.

Figure 6A:
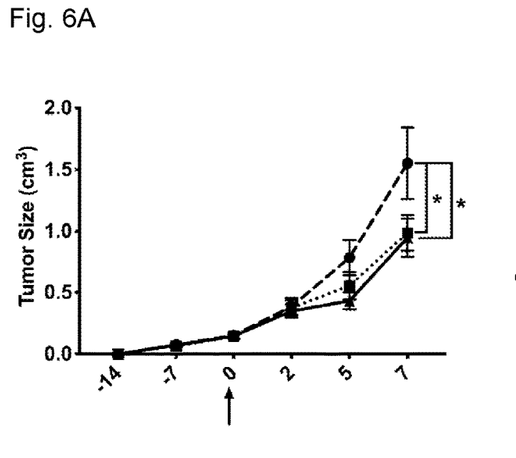
FIGS. 6A-D show evaluation of B16 in C57BL/6J mice.

(A) Top left panel displays injections over time with a new injection at each tick, and tumor size over time.

Figure 6B:
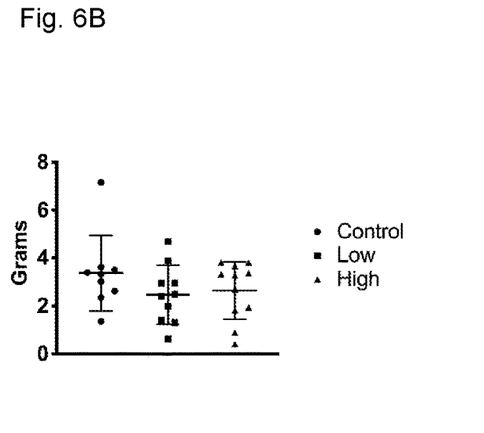

(B) Top right panel displays tumour weight at the end of the study after mice had been euthanized and tumours excised.

Figure 6C:
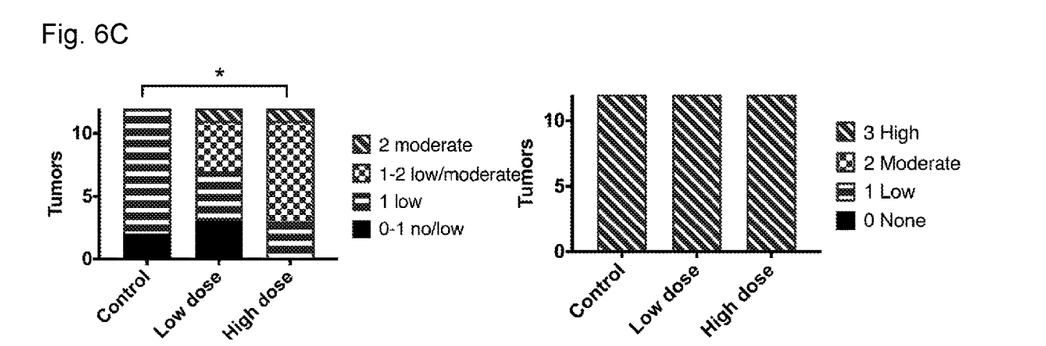

(C) The panel displays histological features of the tumours, these features include lymphocyte invasion (determined by staining for CD3) and degree of necrosis both in the periphery (bottom left) and tumor centre (top left), the degree of necrosis (top right) and the KI67 status of tumors (bottom right).

Figure 6D:
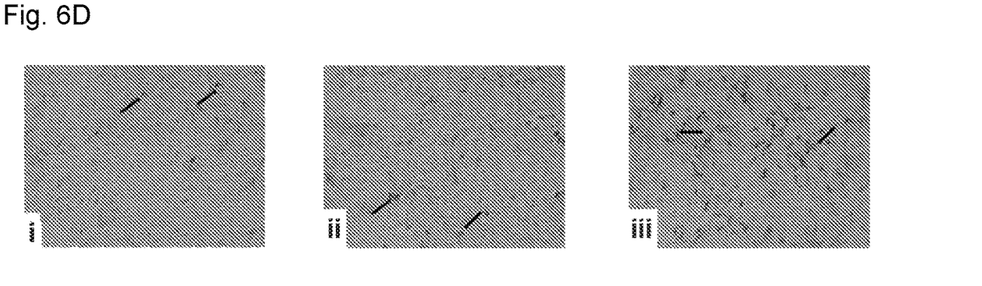

(D) The bottom panel displays histology of tumours stained with CD3, in the control group (A), in the low dose group (B) and in the high dose group (C). The arrows indicate cells that are positively stained for CD3. Five days after the start of injections tumour size was lower in the high dose group when compared to the control (p=0.044 mean 0.34 cm$^3$, CI 95% 0.01-0.69). At the time point of the last injection the tumour size was lower in both the low dose and high dose group (p=0.0017 mean 0.6 cm$^3$ CI 95% 0.27-0.95 and p=0.0006 mean 0.57 cm$^3$ CI 95% 0.22-0.92 respectively). The tumour size when measured after the tumours had been excised did not differ. The amount of CD3+ cells were higher in the high dose group when compared to the control group both in the tumour centre (p=0.017 mean 1.42 rank difference CI 95% 1.09-1.74 vs 2.42 CI 95% 1.78-3.05) and periphery (p=0.003 mean 1.83 rank difference CI 95% 1.59-2.08 vs 2.47 CI 95% 2.47-3.2).

Figures 7A, 7B:
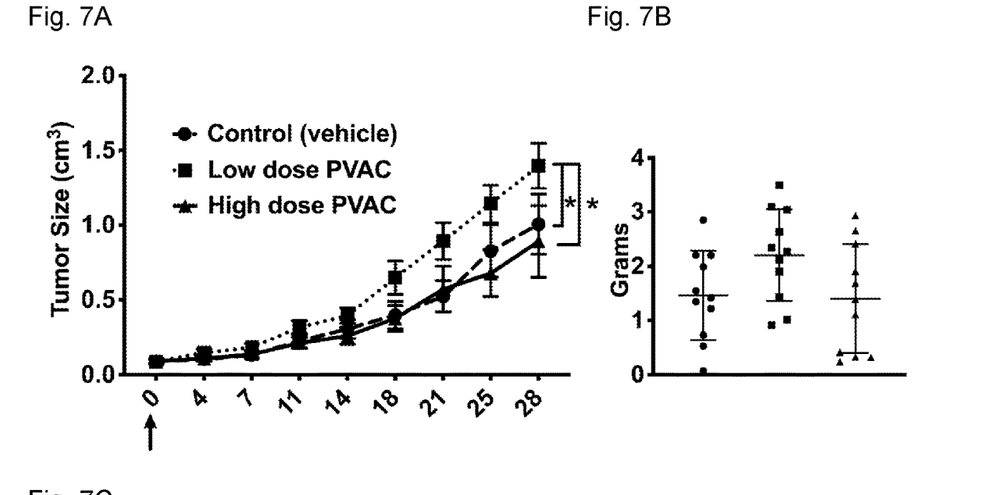
FIGS. 7A-D show evaluation of MDA-MB-231 in athymic nude mice.
Figure 7C:
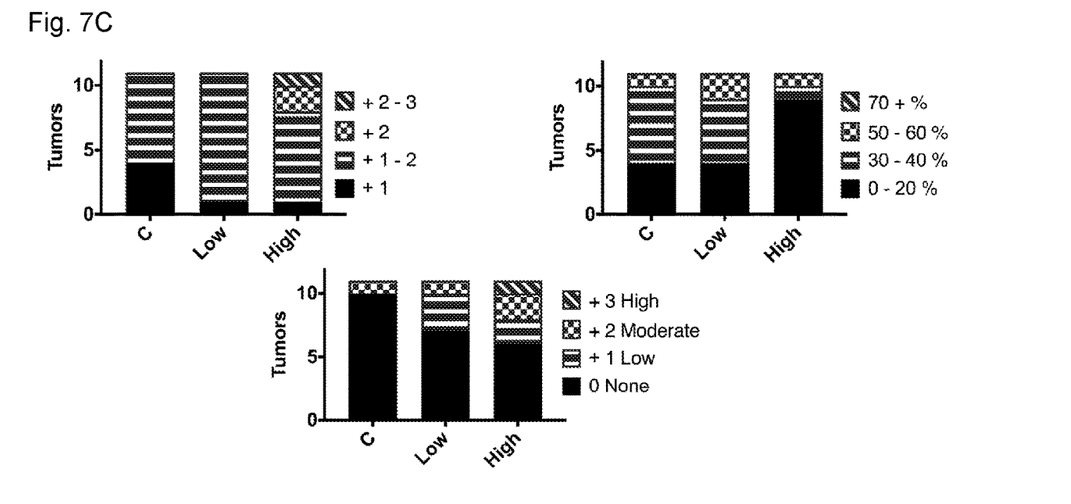
Figure 7D:
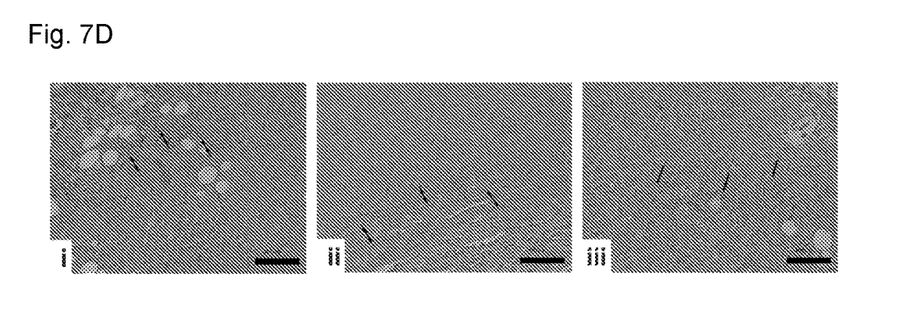

In MDA-MB231 athymic nude mice (FIG. 7), three mice did not develop established tumors and were excluded prior to the treatment period. Three animals, one from each group, were euthanized due to a tumor volume exceeding two mL. Five animals in total were euthanized due to infections, four of these from the PVAC high dose group. PVAC at a low dose resulted in an increased tumor size over time (A), no difference in weight was seen after excision of the tumors (B). No differences were found between the groups for the histological parameters (C) (stromal content (middle), degree of necrosis (right hand) and leukocyte invasion (bottom). The blinded pathology evaluation showed that the high PVAC dose group showed histological signs of a therapeutic effect, described as increased leukocyte counts and more stromal tissue.

4. Discussion

Further to being used in adjunct with conventional chemotherapy agents, polymers have been shown to have direct antitumoral effects, with encouraging results from studies specifically targeting tumor cells with non-toxic effect on normal cells. In addition, its antitumoral effect have been shown in both chemotherapy-resistant cells [5], as well as dormant cancer cells [6], both of which represents major clinical problem in the treatment of cancer. Spurred by this, the inventors sought to determine the effects of a commonly used polymer PVA, functionalized by carbazate groups. It was showed that PVAC potently induced decreased cell viability and leads to late apoptotic/necrotic cell populations (GIST-T1, A375, B16), and, also that either component of PVAC did not exert antitumoral effects. In vivo a statistically significant decrease of tumor growth was observed in the B16.F10 (melanoma) mouse model, also characterized by an increased CD3+ infiltration. This was not observed in the athymic (immune incompetent) mouse model (MDA-MB-13). The non-linear dose relationship observed in the present study is intriguing, that was consistent across all three different cell lines. It has been shown in a model using polymer-based treatment that lower doses increased the apoptotic cell population (14). This could be explained by the prozone or hook effect seen with antibodies (also a drug with multiple binding sites), that agglutination does not appear when antibody is either too high or too low in relation to target. Since PVAC also contains multiple binding sites, this phenomenon could potentially explain the non-linear dose-response relationship. The inventors also showed that the effect was not only time and concentration dependent, but also seeding density dependent. More commonly reported is a low cell density and increased cytotoxicity, likely through higher concentration of the studied drug per cell (15), or more proliferating cells in less densely seeded cells (16).

Since other polymer-based agents have used a membrane disrupting mode of action, a QCM-D approach was used to study whether it had the properties to be able to interact with cell membranes as previously described polymers, however, it was found that PVAC was more hydrophilic than hydrophobic, and in a study assessing its role for membrane-disruption purpose, it was found that when hydrophobic groups decreased in mole-percentage, the antitumoral effect was also decreased (4). Therefore, the inventors believe that PVAC does not act through a membrane disruption mechanism similar to that described for other polymers (4, 5). However, PVAC have been shown to decrease hemolysis in red blood cells (RBCs), which might suggest a membrane-interacting mechanism ([25]. Cell membrane with its lipid rich content, have the ability to form an abundance of reactive carbonyl species (RCS) (17), which is related to disturbed function (18). It is known that cancer produces excess of reactive species. By targeting such species with PVAC, it could be speculated that this leads to a membrane interaction.

Immunotherapy has recently proven itself as a treatment modality within modern oncology. Tumor cells possess the ability to suppress immune cells through several mechanisms (19). To overcome the intra-tumoral tolerance, checkpoint inhibitors (CPI) works by inhibiting suppressive signals, allowing T-cells to become activated (20), which have been proven successful in the treatment of malignant melanoma (21). In the melanoma mouse model used, it was observed an increased CD3+ cell infiltration into the tumor, accompanied by a significant tumor growth inhibition. In clinical samples, tumor-infiltrating lymphocytes have been shown to be a predictive marker for response to CPI treatment (22). In addition, RNA sequencing was performed of the tumor samples, identified genes involved in immune system and inflammatory response, which needs to be further validated. Even though no significant tumor growth inhibition was seen in non-immunocompetent breast cancer mouse model, an increased rate of leukocyte infiltration intratumorally was observed, together with changed histological architecture with increased stromal tissue.

To summarize, polymers have proven to be useful tools, as they can be designed for a wide variety of properties. In this study, a carbazate-activated polyvinyl alcohol was used to determine its antitumoral effects characterized in vitro by decreased cell viability and increased late apoptotic/necrotic cells that could not be observed with either component of PVAC alone. Encouraging findings from in vivo melanoma model which showed apart from tumor growth inhibition also increased lymphocyte infiltration that warrants further study if a possible immunomodulatory capacity of PVAC exists. The treatment was well tolerated in mice, with no obvious toxicity noted. Hence, the present invention discloses a new promising and safe use of PVAC in the prevention, alleviation, and treatment of cancer.

REFERENCES

1. Seymour L W, Ferry D R, Kerr D J, Rea D, Whitlock M, Poyner R, et al. Phase II studies of polymer-doxorubicin (PK1, FCE28068) in the treatment of breast, lung and colorectal cancer. Int J Oncol. 2009; 34(6):1629-36.
2. Dragojevic S, Ryu J S, Raucher D. Polymer-Based Prodrugs: Improving Tumor Targeting and the Solubility of Small Molecule Drugs in Cancer Therapy. Molecules. 2015; 20(12):21750-69.
3. Gakhar G, Liu H, Shen R, Scherr D, Wu D, Nanus D, et al. Anti-tumor effect of novel cationic biomaterials in prostate cancer. Anticancer Res. 2014; 34(8):3981-9.
4. Takahashi H, Yumoto K, Yasuhara K, Nadres E T, Kikuchi Y, Taichman R S, et al. Anticancer polymers designed for killing dormant prostate cancer cells. Sci Rep. 2019; 9(1):1096.
5. Park N H, Cheng W, Lai F, Yang C, Florez de Sessions P, Periaswamy B, et al. Addressing Drug Resistance in Cancer with Macromolecular Chemotherapeutic Agents. J Am Chem Soc. 2018; 140(12):4244-52.
6. Schweizer F. Cationic amphiphilic peptides with cancer-selective toxicity. Eur J Pharmacol. 2009; 625(1-3):190-4.
7. Maeda H, Noguchi Y, Sato K, Akaike T. Enhanced vascular permeability in solid tumor is mediated by nitric oxide and inhibited by both new nitric oxide scavenger and nitric oxide synthase inhibitor. Jpn J Cancer Res. 1994; 85(4):331-4.
8. Maeda H, Wu J, Sawa T, Matsumura Y, Hori K. Tumor vascular permeability and the EPR effect in macromolecular therapeutics: a review. J Control Release. 2000; 65(1-2):271-84.
9. Maeda H. Macromolecular therapeutics in cancer treatment: the EPR effect and beyond. J Control Release. 2012; 164(2):138-44.
10. Maeda H. Polymer therapeutics and the EPR effect. J Drug Target. 2017; 25(9-10):781-5.
11. Maeda H. Tumor-selective delivery of macromolecular drugs via the EPR effect: background and future prospects. Bioconjug Chem. 2010; 21(5):797-802.
12. Tabata Y, Murakami Y, Ikada Y. Tumor accumulation of poly(vinyl alcohol) of different sizes after intravenous injection. J Control Release. 1998; 50(1-3):123-33.
13. Meister A, Anderson M E. Glutathione. Annu Rev Biochem. 1983; 52:711-60.
14. Jeong H, Hwang J, Lee H, Hammond P T, Choi J, Hong J. In vitro blood cell viability profiling of polymers used in molecular assembly. Sci Rep. 2017; 7(1):9481.
15. Lee Y C, Chuang C Y, Lee P K, Lee J S, Harper R W, Buckpitt A B, et al. TRX-ASK1-JNK signaling regulation of cell density-dependent cytotoxicity in cigarette smoke-exposed human bronchial epithelial cells. Am J Physiol Lung Cell Mol Physiol. 2008; 294(5): L921-31.
16. Caviglia C, Zór K, Canepa S, Carminati M, Larsen L B, Raiteri R, et al. Interdependence of initial cell density, drug concentration and exposure time revealed by real-time impedance spectroscopic cytotoxicity assay. Analyst. 2015; 140(10):3623-9.
17. Fritz K S, Petersen D R. An overview of the chemistry and biology of reactive aldehydes. Free Radic Biol Med. 2013; 59:85-91.
18. Schopfer F J, Cipollina C, Freeman B A. Formation and signaling actions of electrophilic lipids. Chem Rev. 2011; 111(10):5997-6021.
19. Rabinovich G A, Gabrilovich D, Sotomayor E M. Immunosuppressive strategies that are mediated by tumor cells. Annu Rev Immunol. 2007; 25:267-96.
20. Wei S C, Duffy C R, Allison J P. Fundamental Mechanisms of Immune Checkpoint Blockade Therapy. Cancer Discov. 2018; 8(9):1069-86.
21. Larkin J, Chiarion-Sileni V, Gonzalez R, Grob J J, Rutkowski P, Lao C D, et al. Five-Year Survival with Combined Nivolumab and Ipilimumab in Advanced Melanoma. N Engl J Med. 2019.
22. Chen P L, Roh W, Reuben A, Cooper Z A, Spencer C N, Prieto P A, et al. Analysis of Immune Signatures in Longitudinal Tumor Samples Yields Insight into Biomarkers of Response and Mechanisms of Resistance to Immune Checkpoint Blockade. Cancer Discov. 2016; 6(8):827-37.
23. DeMerlis C C, Schoneker D R. Review of the oral toxicity of polyvinyl alcohol (PVA). Food Chem Toxicol Int J Publ Br Ind Biol Res Assoc. 2003 March; 41(3): 319-26.
24. Yamaoka T, Tabata Y, Ikada Y. Comparison of Body Distribution of Poly(vinyl alcohol) with Other Water-soluble Polymers after Intravenous Administration. J Pharm Pharmacol. 1995 Jun. 1; 47(6):479-86.
25. F. Fredriksson et al. Sutures impregnated with carbazate-activated polyvinyl alcohol reduce intraperitoneal adhesions (2017), J. of paediatric surgery 52, pp. 1853-1858 (2017).

The invention claimed is:

1. A method for alleviating and/or treating cancer in a subject comprising administering a therapeutically effective amount of a polymer comprising a carbazate-modified polyvinyl alcohol (PVAC) of Formula I, Formula I wherein, unmodified repeat units of PVA are denoted with n and carbazate groups conjugated to repeat units are denoted by m, to a subject in need of such treatment.

2. The method according to claim 1, wherein the cancer is selected from melanoma, gastrointestinal cancer, T-cell lymphoma, B-cell lymphoma and Hedgin's lymphoma.

3. The method according claim 1, wherein the administration is performed by intravenous, intramuscular, intraperitoneal, or subcutaneous injection or infusion.

4. The method according to claim 1 in combination with another anticancer treatment.

5. The method according to claim 1, wherein the polymer has a degree of polymerization in the range of $100<DP<2000$.

6. The method according to claim 1, wherein the polymer has a degree of substitution (DS) of carbazide in the range of 0.5-50%.

7. The method according to claim 1, wherein the polymer has a carbazate content in the range of 0.1-10 mmol/g polyvinyl alcohol carbazate.

* * * * *